(12) United States Patent
Feldman et al.

(45) Date of Patent: Jun. 21, 2022

(10) Patent No.: US 11,364,382 B2

(54) PASSIVE CHARGE RECOVERY CIRCUITRY FOR AN IMPLANTABLE MEDICAL DEVICE

(71) Applicant: Boston Scientific Neuromodulation Corporation, Valencia, CA (US)

(72) Inventors: Emanuel Feldman, Simi Valley, CA (US); Goran N. Marnfeldt, Valencia, CA (US); Jordi Parramon, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 67 days.

(21) Appl. No.: 16/930,817

(22) Filed: Jul. 16, 2020

(65) Prior Publication Data

US 2020/0346007 A1    Nov. 5, 2020

Related U.S. Application Data

(63) Continuation of application No. 15/695,999, filed on Sep. 5, 2017, now Pat. No. 10,716,937.

(Continued)

(51) Int. Cl.
*A61N 1/37* (2006.01)
*A61N 1/36* (2006.01)

(Continued)

(52) U.S. Cl.
CPC .............. *A61N 1/36* (2013.01); *A61N 1/025* (2013.01); *A61N 1/05* (2013.01); *A61N 1/36125* (2013.01);

(Continued)

(58) Field of Classification Search
CPC ... A61N 1/36125; A61N 1/3716; A61N 1/362
See application file for complete search history.

(56) References Cited

U.S. PATENT DOCUMENTS 5,725,560 A    3/1998  Brink
6,181,969 B1   1/2001  Gord
(Continued)

FOREIGN PATENT DOCUMENTS

WO    2016/081096 A1    5/2016

OTHER PUBLICATIONS

Sooksood K, et al., "An Experimental Study on Passive Charge Balancing," Adv. Radio Sci., 7, 2009, pp. 197-200.
(Continued)

*Primary Examiner* — George R Evanisko
(74) *Attorney, Agent, or Firm* — Lewis & Reese, PLLC

(57) ABSTRACT

Recovery circuitry for passively recovering charge from capacitances at electrodes in an Implantable Pulse Generator (IPG) is disclosed. The passive recovery circuitry includes passive recovery switches intervening between each electrode node and a common reference voltage, and each switch is in series with a variable resistance that may be selected based on differing use models of the IPG. The passive recovery switches may also be controlled in different modes. For example, in a first mode, the only recovery switches closed after a stimulation pulse are those associated with electrodes used to provide stimulation. In a second mode, all recovery switches are closed after a stimulation pulse, regardless of the electrodes used to provide stimulation. In a third mode, all recovery switches are closed continuously, which can provide protection when the IPG is in certain environments (e.g., MRI), and which can also be used during stimulation therapy itself.

16 Claims, 13 Drawing Sheets

Related U.S. Application Data

(60) Provisional application No. 62/393,007, filed on Sep. 10, 2016.

(51) Int. Cl.
*A61N 1/02* (2006.01)
*A61N 1/05* (2006.01)

(52) U.S. Cl.
CPC ....... *A61N 1/36128* (2013.01); *A61N 1/3716* (2013.01)

(56) References Cited

U.S. PATENT DOCUMENTS

| | | |
|---|---|---|
| 6,516,227 B1 | 2/2003 | Meadows et al. |
| 6,553,263 B1 | 4/2003 | Meadows et al. |
| 6,633,780 B1 * | 10/2003 | Berger ................ A61N 1/0563 607/119 |
| 7,127,298 B1 | 10/2006 | He et al. |
| 7,177,698 B2 | 2/2007 | Klosterman et al. |
| 7,389,140 B1 | 6/2008 | Kroll |
| 7,444,181 B2 | 10/2008 | Shi et al. |
| 7,539,538 B2 | 5/2009 | Parramon et al. |
| 7,623,916 B2 | 11/2009 | Julian |
| 7,801,600 B1 | 9/2010 | Carbunaru et al. |
| 7,801,602 B2 | 9/2010 | McClure et al. |
| 7,872,884 B2 | 1/2011 | Parramon et al. |
| 7,881,803 B2 | 2/2011 | Parramon et al. |
| 7,890,182 B2 | 2/2011 | Parramon et al. |
| 8,369,963 B2 * | 2/2013 | Parramon .......... A61N 1/36125 607/61 |
| 8,606,362 B2 | 12/2013 | He et al. |
| 8,620,436 B2 | 12/2013 | Parramon et al. |
| 8,649,858 B2 | 2/2014 | Griffith et al. |
| 8,768,453 B2 | 7/2014 | Parramon et al. |
| 9,002,465 B2 | 4/2015 | Rann |
| 9,008,790 B2 | 4/2015 | Griffith et al. |
| 9,037,241 B2 | 5/2015 | Lamont et al. |
| 9,061,140 B2 | 6/2015 | Shi et al. |
| 9,155,891 B2 | 10/2015 | Archer |
| 9,174,051 B2 | 11/2015 | Marnfeldt et al. |
| 9,220,901 B2 | 12/2015 | Gururaj et al. |
| 9,233,254 B2 | 1/2016 | Nimmagadda et al. |
| 9,259,574 B2 | 2/2016 | Aghassian et al. |
| 9,308,373 B2 | 4/2016 | Lee |
| 9,314,632 B2 | 4/2016 | Marnfeldt et al. |
| 9,327,135 B2 | 5/2016 | Vansickle et al. |
| 9,352,162 B2 | 5/2016 | Lamont et al. |
| 9,397,639 B2 | 7/2016 | Feldman et al. |
| 2006/0173493 A1 | 8/2006 | Armstrong et al. |
| 2008/0097529 A1 * | 4/2008 | Parramon .......... A61N 1/36125 607/2 |
| 2008/0228236 A1 | 9/2008 | Varrichio et al. |
| 2010/0125315 A1 | 5/2010 | Parramon et al. |
| 2010/0268309 A1 * | 10/2010 | Parramon .......... A61N 1/3686 607/116 |
| 2012/0095529 A1 | 4/2012 | Parramon et al. |
| 2013/0184794 A1 | 7/2013 | Feldman et al. |
| 2015/0134029 A1 | 5/2015 | Ozawa et al. |
| 2015/0144183 A1 | 5/2015 | Yang et al. |
| 2015/0157861 A1 | 6/2015 | Aghassian |
| 2016/0051825 A1 | 2/2016 | Ter-Petrosyan et al. |

OTHER PUBLICATIONS

Sooksood K, et al., "Recent Advances in Charge Balancing for Functional Electrical Stimulation," 31st Annual International Conference of the IEEE, 2009, 4 pages.

* cited by examiner

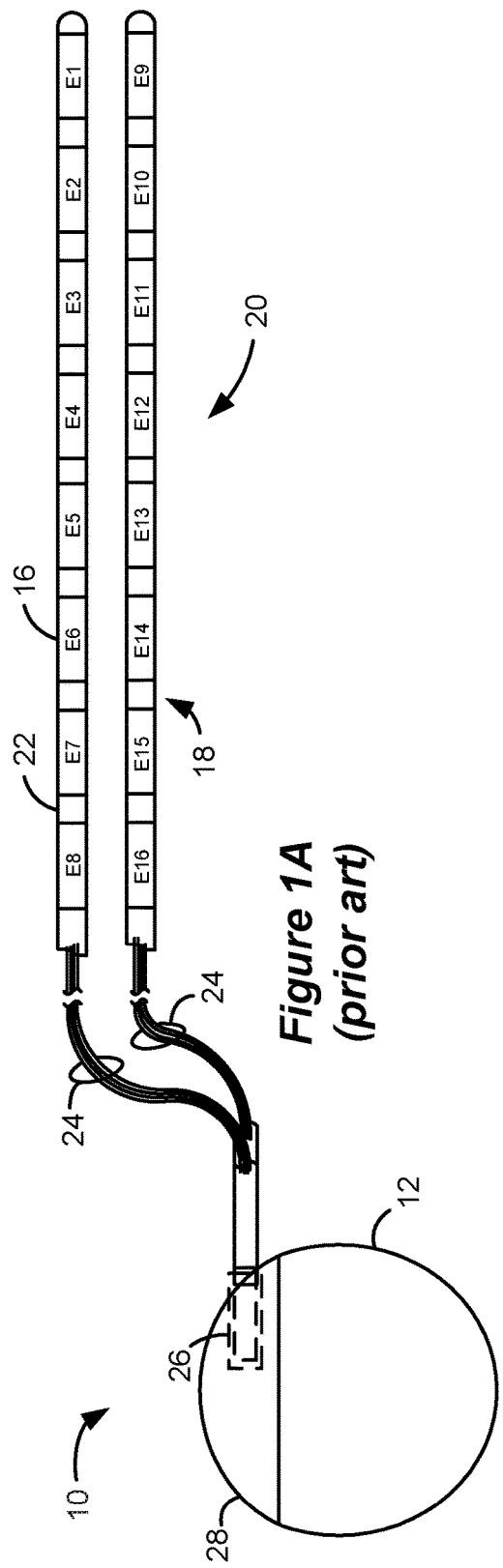
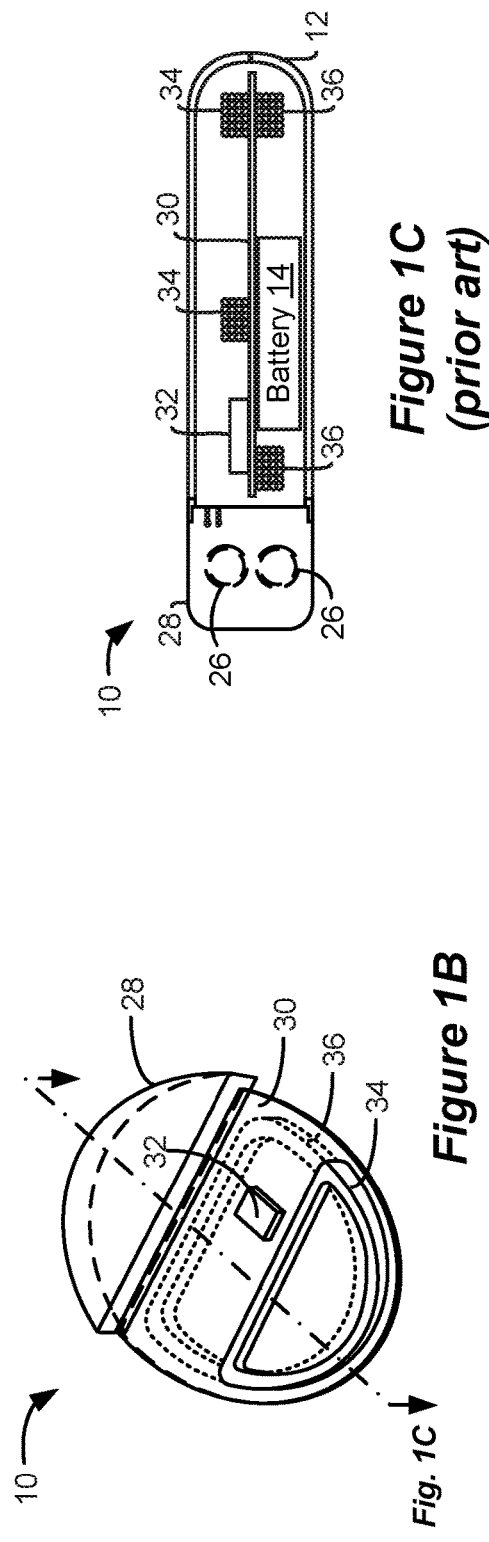
*Figure 1A (prior art)*
*Figure 1B (prior art)*
*Figure 1C (prior art)*

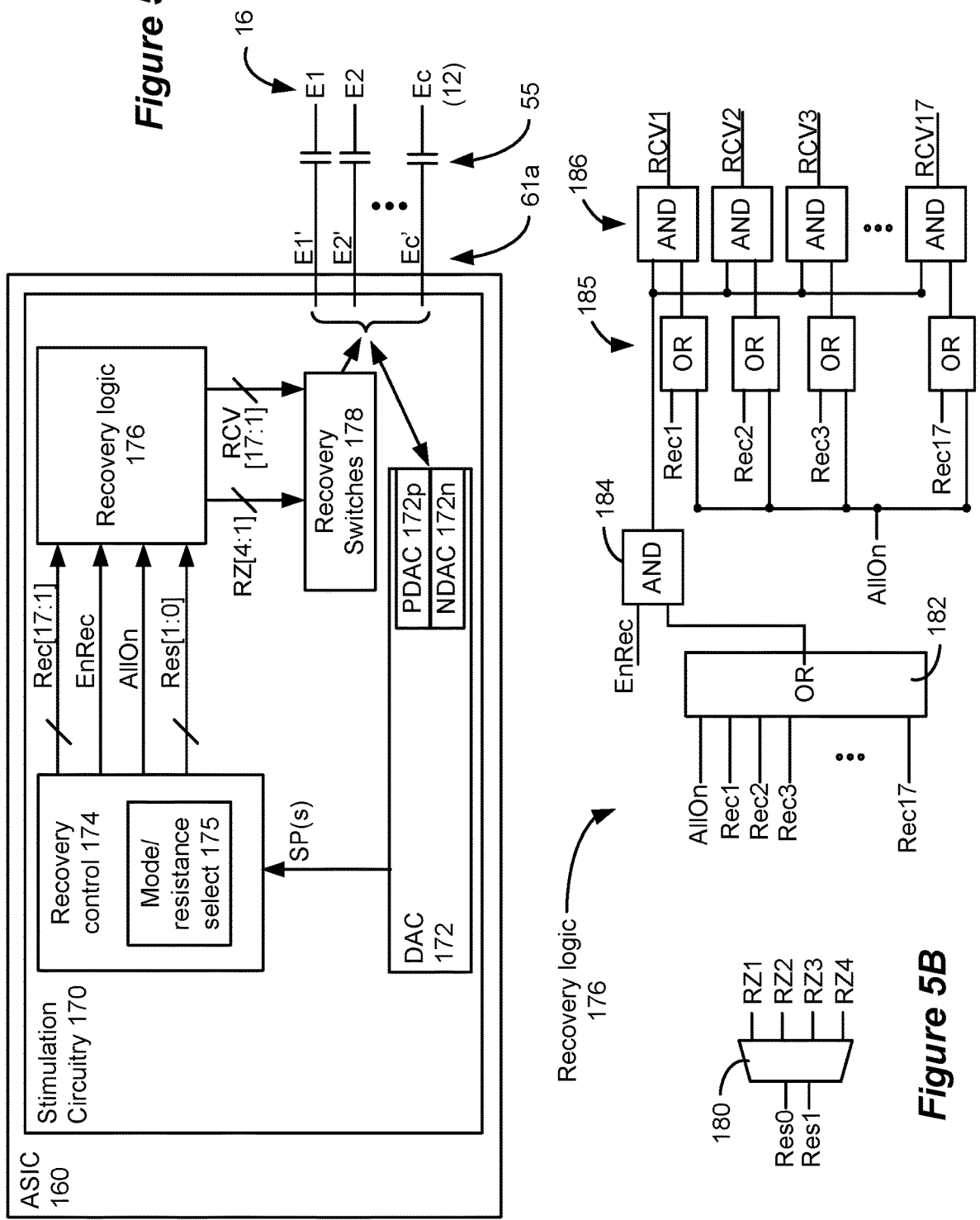

| Mode | EnRec | AllOn | Rec[1:17] | Resistance | | | |
|---|---|---|---|---|---|---|---|
| | | | | RZ=1 (50Ω) | RZ=2 (300Ω) | RZ=3 (1.8kΩ) | RZ=4 (10kΩ) |
| Recovery of selected electrodes | '1' | '0' | Individually asserted during recovery period | High freq. stim. | Low freq. stim. | | |
| Recovery of all electrodes | '1' | '0' | All asserted during recovery period | More than one channel of stimulation | | | |
| | '1' | Asserted during recovery period | n/a | More than one channel of stimulation | | | |
| Recovery switches on semi-permanetly | '1' | '1' | n/a | Electro-cautery; MRI | | | Continuous recovery during stimulation (high freq.) |

*Figure 6*

PASSIVE CHARGE RECOVERY CIRCUITRY FOR AN IMPLANTABLE MEDICAL DEVICE

CROSS REFERENCE TO RELATED APPLICATIONS

This is a continuation application of U.S. patent application Ser. No. 15/695,999, filed Sep. 5, 2017, which is a non-provisional application based on U.S. Provisional Patent Application Ser. No. 62/393,007, filed Sep. 10, 2016. These applications are incorporated by reference in its entirety, and priority to them is claimed.

FIELD OF THE INVENTION

The present invention relates generally to implantable medical devices, and more particularly to improved passive charge recovery circuitry for an implantable pulse generator.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller (not shown); and a charging coil 36 for charging or recharging the IPG's battery 14 using an external charger (not shown). FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIG. 2A shows a prior art architecture 40 for the circuitry in IPG 10, which is disclosed in U.S. Patent Application Publications 2012/0095529, 2012/0092031 and 2012/0095519 ("ASIC Publications"), which are incorporated by reference in their entireties. Architecture 40 includes a microcontroller integrated circuit 50 and an Application Specific Integrated Circuit (ASIC) 60 in communication with each other by a bus 90. Stated simply, the microcontroller 50 provides master control for the architecture 40, while ASIC 60 takes commands from and provides data to the microcontroller. ASIC 60 provides specific IPG functionality. For example, and as explained in further detail below, ASIC 60 send stimulation current to and reads measurements from the sixteen electrodes 16. ASIC 60 comprises a mixed mode IC carrying and processing both analog and digital signals, whereas microcontroller 50 comprises a digital IC carrying and processing only digital signals.

Microcontroller 50 and ASIC 60 comprise monolithic integrated circuits each formed on their own semiconductive substrates ("chips"), and each may be contained in its own package and mounted to the IPG 10's PCB 30. Architecture 40 may also include additional memory (not shown) for storage of programs or data beyond that provided internally in the microcontroller 50. Additional memory may be connected to the microcontroller 50 by a serial interface (SI) as shown, but could also communicate with the microcontroller 50 via bus 90. Bus 90 may comprise a parallel address/data bus, and may include a clock signal and various control signals to dictate reading and writing to various memory locations, as explained in the '529 Publication. Bus 90 and the signals it carries may also take different forms; for example, bus 90 may include separate address and data lines, may be serial in nature, etc.

As explained in the above-referenced ASIC Publications, architecture 40 is expandable to support use of a greater number of electrodes 16 in the IPG 10. For example, and as shown in dotted lines in FIG. 2A, architecture 40 may include another ASIC 60' identical in construction to ASIC 60, thus expanding the number of electrodes supported by the IPG 10 from sixteen to thirty two. Various off-bus connections 54 (i.e., connections not comprising part of bus 90) can facilitate such expansion, and may further (e.g., by bond programming; see inputs M/S) designate ASIC 60 as a master and ASIC 60' as a slave. Such differentiation between the ASICs 60 and 60' can be useful, as certain redundant functionality in the slave ASIC 60' can be disabled in favor of the master ASIC 60. Off-bus communications 54 can allow the voltage at the electrodes nodes 61a (E1'-E16') of one of the ASICs (60'; OUT1, OUT2) to be sent to the other ASIC (60; IN1, IN2) to be measured. Off-bus connections 54 are further useful in generation and distribution of a clock signal governing communications on the bus 90 as well as in the ASIC(s) 60. As these concepts are discussed in detail in the above-referenced ASIC Publications, they are not elaborated upon here.

FIG. 2B shows various functional circuit blocks within ASIC 60, which are briefly described. ASIC 60 includes an internal bus 92 which can couple to external bus 90 and which may duplicate bus 90's signals. Note that each of the functional blocks includes interface circuitry 88 enabling communication on the internal bus 92 and ultimately external bus 90, as the above-referenced ASIC Publications explain. Interface circuitry 88 includes circuitry to help each block recognize when bus 92 is communicating data with addresses belonging to that block. ASIC 60 contains several terminals 61 (e.g., pins, bond pads, solder bumps, etc.), such as those necessary to connect to the bus 90, the battery 14, the coils 34, 36, external memory (not shown). Terminals 61 include electrode node terminals 61a (E1'-E16') which connect to the electrodes 16 (E1-E16) on the lead(s) 18 by way of DC-blocking capacitors 55. As is known, DC-blocking capacitors 55 are useful to ensure that DC current isn't inadvertently (e.g., in the event of failure of the ASIC 60's circuitry) injected into the patient's tissue, and hence provide safety to the IPG 10. Such DC-blocking capacitors 55 can be located on or in the IPG 10's PCB 30 (FIG. 1C) inside of the IPG's case 12. See U.S. Patent Application Publication 2015/0157861.

Each of the circuit blocks in ASIC 60 performs various functions in IPG 10. Telemetry block 64 couples to the IPG telemetry coil 34, and includes transceiver circuitry for wirelessly communicating with an external device according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 38, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat or voltages appearing at the electrodes, and is coupled to an analog bus 67 containing such voltages. A/D block 66 may further receive signals from sample and hold block 68, which as the ASIC Publications explain can be used to measure such voltages, or differences between two voltages. For example, sample and hold circuitry 68 may receive voltages from two electrodes and provide a difference between them (see, e.g., Ve1-Ve2 in FIG. 3, discussed subsequently), which difference voltage may then be digitized at A/D block 66. Knowing the difference in voltage between two electrodes when they pass a constant current allows for a determination of the (tissue) resistance between them, which is useful for a variety of reasons.

Sample and hold block 68 may also be used to determine one or more voltage drops across the DAC circuitry 72 used to create the stimulation pulses (see, e.g., Vp and Vn in FIG. 3, explained subsequently). This is useful to setting the compliance voltage V+ to be output by a compliance voltage generator block 76. Compliance voltage V+ powers the DAC circuitry 72, and the measured voltage drops ensure that the compliance voltage V+ produced is optimal for the stimulation current to be provided—i.e., V+ is not too low as to be unable to produce the current required for the stimulation, nor too high so as to waste power in the IPG 10. Compliance voltage generator block 76 includes circuitry for boosting a power supply voltage such as the battery voltage, Vbat, to a proper level for V+. Such circuitry (some of which may be located off chip) can include an inductor-based boost converter or a capacitor-based charge pump, which are described in detail in U.S. Patent Application Publication 2010/0211132.

Clock generation block 74 can be used to generate a clock for the ASIC 60 and communication on the bus. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 60.

Master/slave control block 86 can be used to inform the ASIC 60 whether it is to be used as a master ASIC or as a slave ASIC (e.g., 60'), which may be bond programmed at M/S terminal 61. For example, M/S terminal may be connected to a power supply voltage (e.g., Vbat) to inform ASIC 60 that it will operate as a master ASIC, or to ground to inform that it will operate as a slave, in which case certain function blacks will be disabled, as the ASIC Publications explain.

Interrupt controller block 80 receives various interrupts (e.g., INT1-INT4) from other circuit blocks, which because of their immediate importance are received independent of the bus 92 and its communication protocol. Interrupts may also be sent to the microcontroller 50 via the bus 90. Internal controller 82 in the ASIC 60 may receive indication of such interrupts, and act a controller for all other circuit blocks, to the extent microcontroller 50 (FIG. 2A) does not handle such interrupt through the external bus 90. Further, each of the functional circuit blocks contain set-up and status registers (not shown) written to by the controller 82 upon initialization to configure and enable each block. Each functional block can then write pertinent data at its status registers, which can in turn be read by the controller 82 via internal bus 92 as necessary, or by the microcontroller 50 via external bus 90. The functional circuit blocks can further simple state machines to manage their operation, which state machines are enabled and modified via each block's set-up and status registers.

Nonvolatile memory (NOVO) block 78 caches any relevant data in the system (such as log data). Additional memory (not shown) can also be provided off-chip via a serial interface block 84.

ASIC 60 further includes a stimulation circuit block 70, which includes circuitry for receiving and storing stimulation parameters from the microcontroller 50 via buses 90 and 92. Stimulation parameters define the shape and timing of stimulation pulses to be formed at the electrodes, and can include parameters such as which electrodes E1-E16 will be active; whether those active electrodes are to act as anodes that source current to a patient's tissue, or cathodes that sink current from the tissue; and the amplitude (A), duration (d), and frequency (f) of the pulses. Amplitude may comprise a voltage or current amplitude. Such stimulation parameters may be stored in registers in the stimulation circuitry block 70. See, e.g., U.S. Patent Application Publications 2013/0289661; 2013/0184794.

Block 70 also includes a Digital-to-Analog Converter (DAC) 72 for receiving the stimulation parameters from the registers and for forming the prescribed pulses at the selected electrodes. FIG. 3 shows a simple example of DAC circuitry 72 as used to provide a current pulse between selected electrodes E1 and E2 and through a patient's tissue, Rt. DAC circuitry 72 as shown comprises two portions, denoted as PDAC 72p and NDAC 72n. These portions of DAC circuitry 72 are so named because of the polarity of the transistors used to build them and the polarity of the current they provide. Thus, PDAC 72p is formed from P-channel transistors and is used to source a current +I to the patient's tissue Rt via a selected electrode E1 operating as an anode. NDAC 72n is formed of N-channel transistors and is used to sink current −I from the patient's tissue via a selected electrode E2. It is important that current sourced to the tissue at any given time equal that sunk from the tissue to prevent charge from building in the tissue, although more than one anode electrode and more than one cathode electrode may be operable at a given time.

PDAC 72p and NDAC 72n receive digital control signals from the registers in the stimulation circuitry block 70, denoted <Pstim> and <Nstim> respectively, to generate the prescribed pulses with the prescribed timing. In the example shown, PDAC 72p and NDAC 72n comprise current sources, and in particular include current-mirrored transistors for mirroring (amplifying) a reference current Iref to produce pulses with an amplitude (A) of I. PDAC 72p and NDAC 72n could however also comprise constant voltage sources. Control signals <Pstim> and <Nstim> also prescribe the timing of the pulses, including their duration (D) and frequency (f), as shown in the waveforms generated at the selected electrodes. The PDAC 72p and NDAC 72n along with the intervening tissue Rt complete a circuit between a power supply V+—the compliance voltage as already introduced—and ground. As noted earlier, the compliance voltage V+ is adjustable to an optimal level at compliance voltage generator block 76 (FIG. 2B) to ensure that current pulses of a prescribed amplitude can be produced without unnecessarily wasting IPG power.

The DAC circuitry 72 (PDAC 72p and NDAC 72n) may be dedicated at each of the electrodes, and thus may be activated only when its associated electrode is to be selected as an anode or cathode. See, e.g., U.S. Pat. No. 6,181,969. Alternatively, one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 72p or NDAC 72n. See, e.g., U.S. Pat. No. 8,606,362. DAC circuitry 72 may also use a combination of these dedicated and distributed approaches. See, e.g., U.S. Pat. No. 8,620,436.

In the example waveform shown, the pulses provided at the electrodes are biphasic, meaning that each pulse comprises a first phase 94a of a first polarity, followed by a second phase 94b of an opposite polarity. This is useful as a means of active recovery of charge that may build up on the DC-blocking capacitors 55. Thus, while charge will build up on the capacitors 55 during the first pulse phase 94a, the second pulse phase 94b will actively recover that charge, particularly if the total amount of charge is equal in each phase (i.e., of the area under the first and second pulse phases are equal). Recovery of excess charge on the DC-blocking capacitors 55 is important to ensure that the DAC circuit 72 will operate as intended: if the charge/voltage across the DC-blocking capacitors 55 is not zero at the end of each pulse, remaining charge/voltage will skew formation of subsequent pulses, which may therefore not provide the prescribed amplitude.

While active recovery of charge using a biphasic pulse is beneficial, such active recovery may not be perfect, and hence some residual charge may remain on the DC-blocking capacitors 55 even after the second phase 94b of the biphasic pulse. Thus, the art has recognized the utility of passive charge recovery. Passive charge recovery is implemented with the stimulation circuit block 70, and includes use of passive recovery switches (transistors) 96, which are connected between the electrode nodes (E1'-E16') 61a and a common reference voltage. This voltage as shown may simply comprise the battery voltage, Vbat, but another common reference voltage could also be used. Closing the passive recovery switches 96 during a time period 98 after the second pulse phase 94b couples the DC-blocking capacitors 55 in parallel between the reference voltage and the patient's tissue. Given the previous serial connection of the DC-blocking capacitors, this should normalize any remaining charge.

BRIEF DESCRIPTION OF THE DRAWINGS

FIGS. 1A-1C show an Implantable Pulse Generator (IPG), and the manner in which an electrode array is coupled to the IPG, in accordance with the prior art.

FIGS. 5A-5C show improved passive recovery circuitry operable in different modes and at different resistances, in accordance with an example of the invention.

FIG. 6 shows a table illustrating how the different modes and resistances are enabled, and stimulation use models in which the different modes and resistances can be used, in accordance with an example of the invention.

DETAILED DESCRIPTION

Figure 4A:
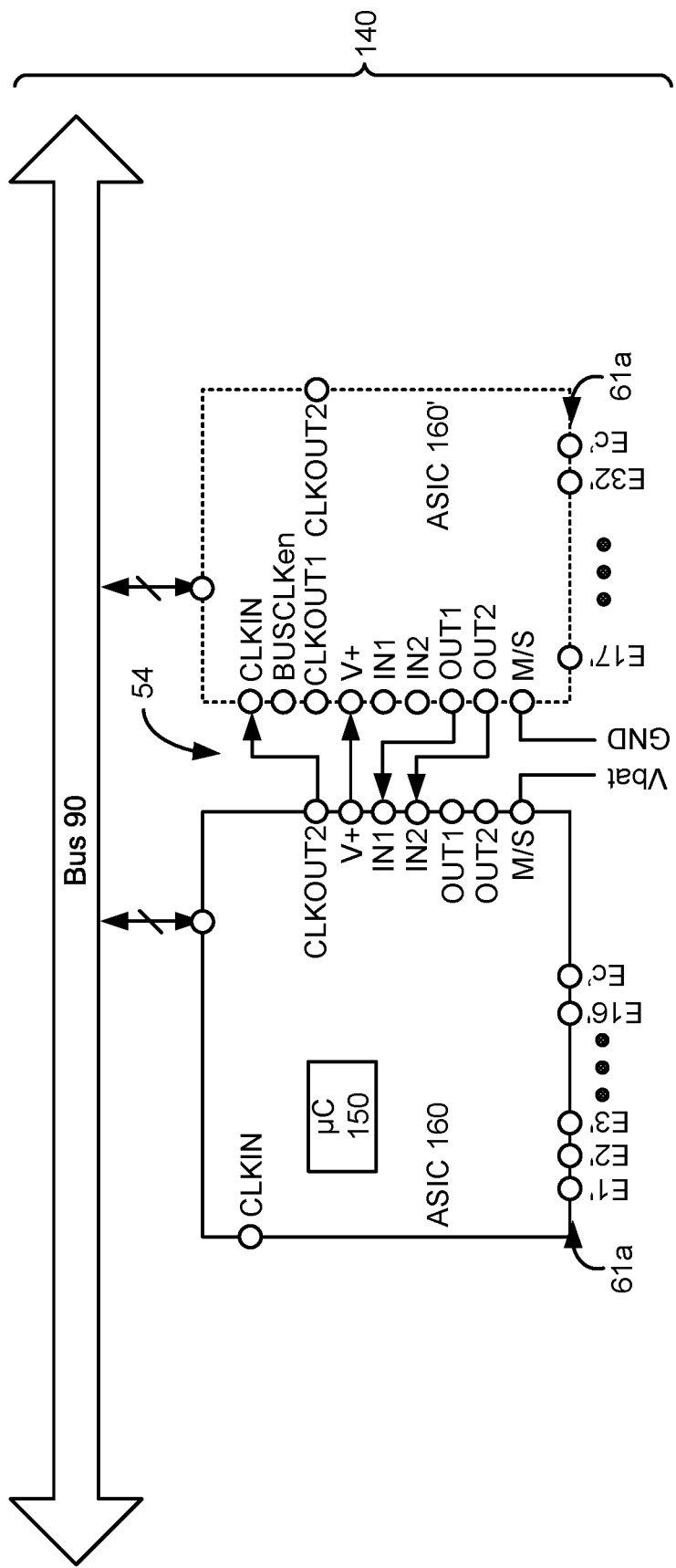
FIG. 4A shows an improved architecture for an IPG, in which an improved ASIC includes a microcontroller, in accordance with an example of the invention.
Figure 4B:
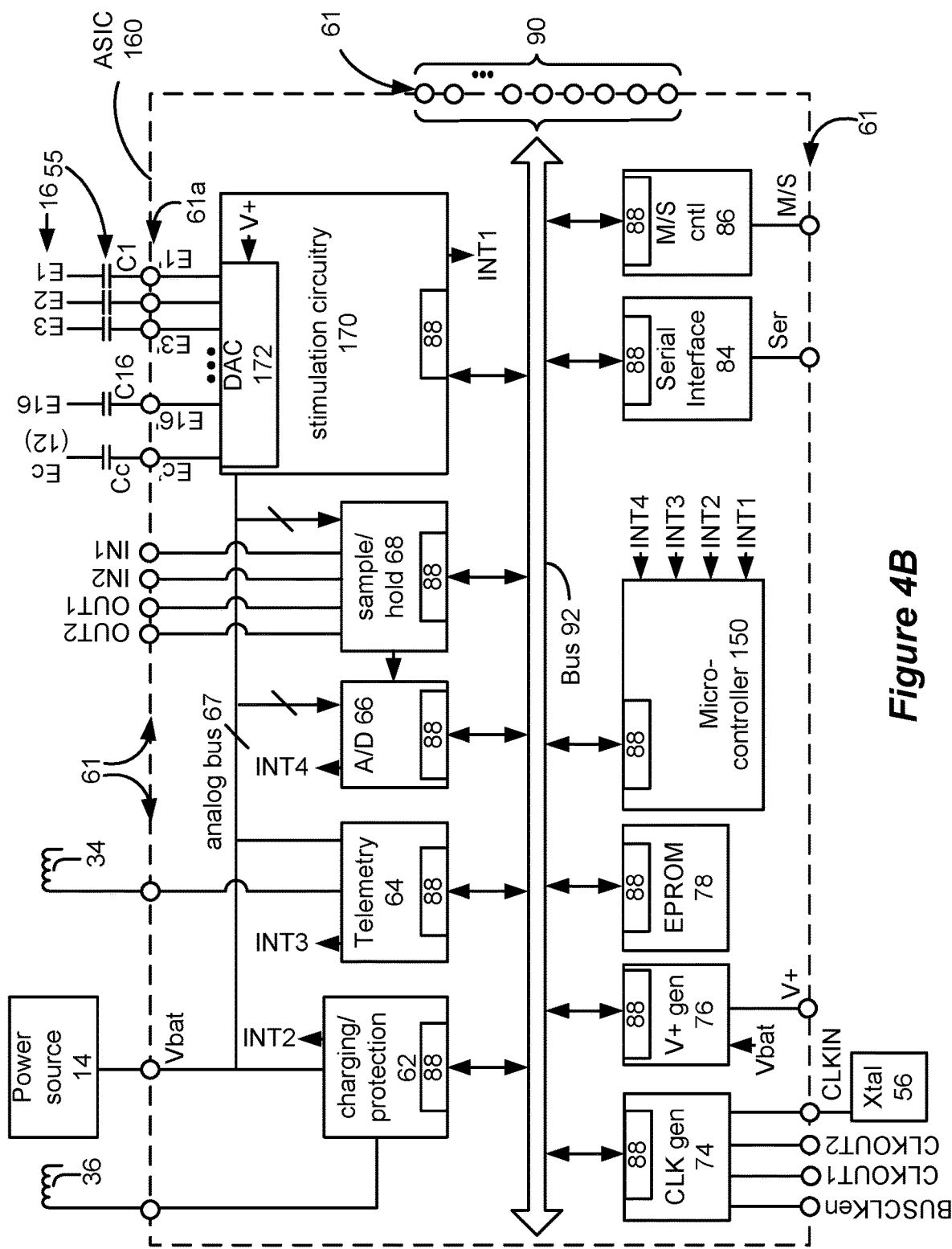
FIG. 4B shows circuitry blocks within the improved ASIC, in accordance with an example of the invention.

FIGS. 4A and 4B show an improved architecture 140 and ASIC 160 for an IPG such as IPG 10 described earlier. Elements in architecture 140 and ASIC 160 that can remain unchanged from the prior art architecture 40 and ASIC 60 described in the Background bear the same elements numerals, and are not described again.

Figure 2A:
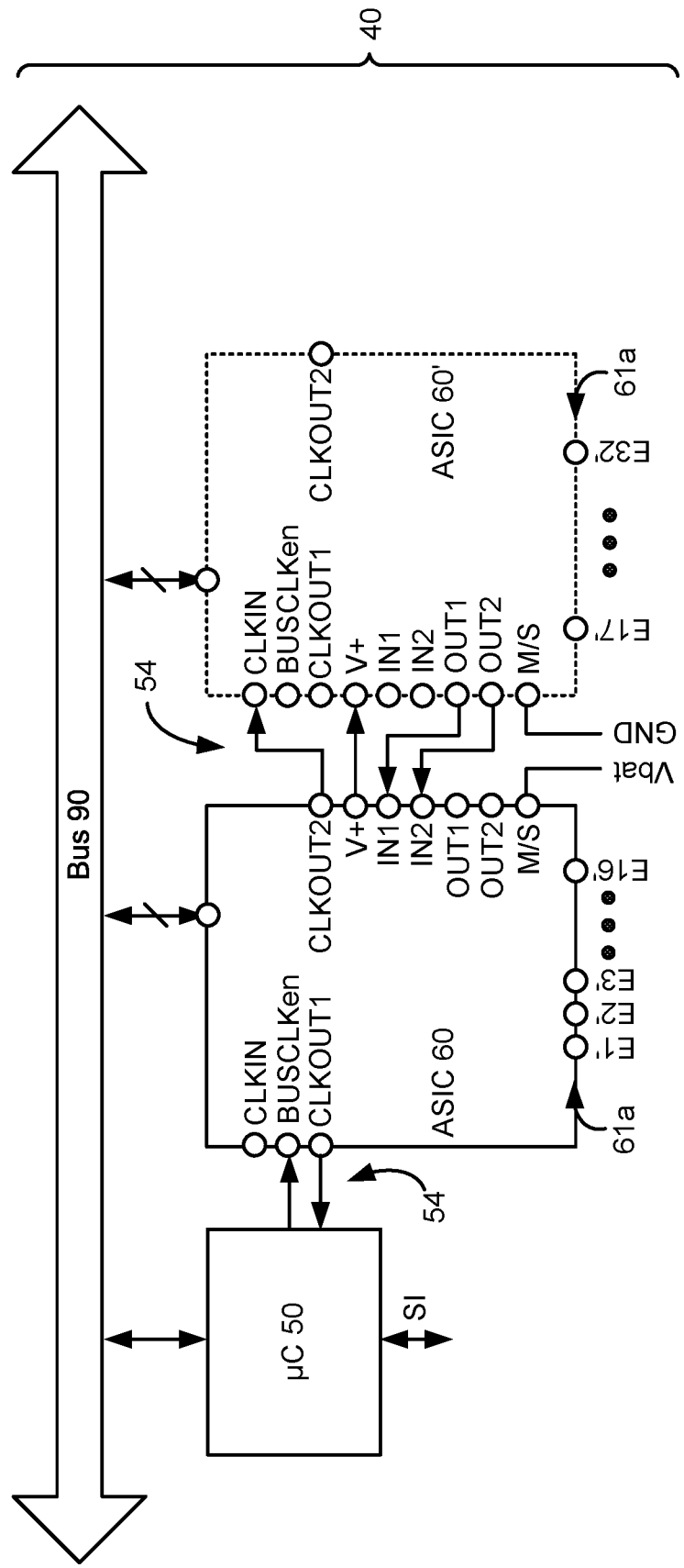
FIG. 2A shows an architecture for an IPG utilizing a microcontroller integrated circuit and an Application Specific Integrated Circuit (ASIC), in accordance with the prior art.
Figure 2B:
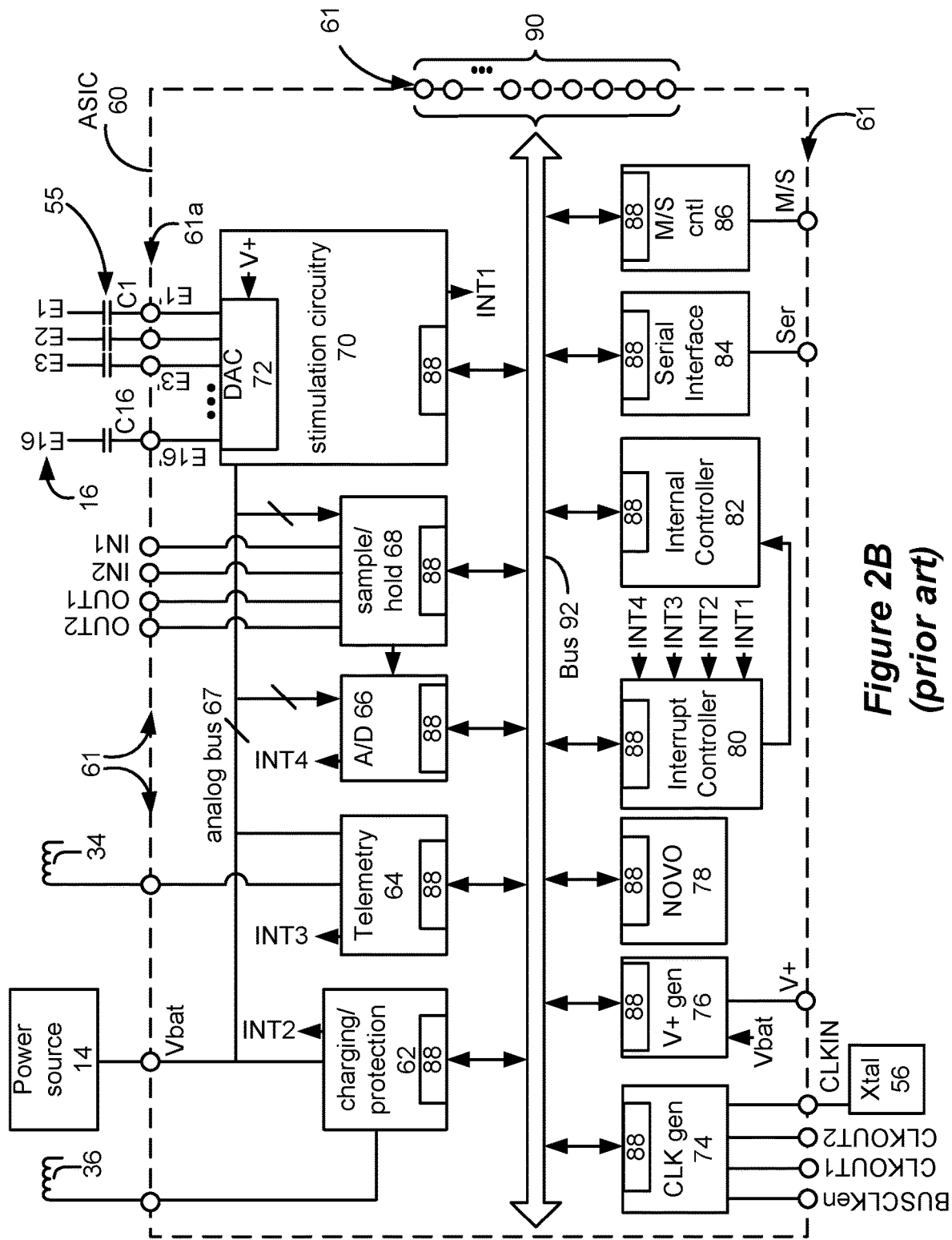
FIG. 2B shows circuitry blocks within the ASIC, and connection to off-chip components, in accordance with the prior art.

Improved ASIC 160 includes a microcontroller block 150 as part of its monolithic structure, which as shown in FIG. 4B can communicate with other functional blocks in the ASIC 160 via internal bus 92. Because ASIC 160 includes an internal microcontroller 150, an external microcontroller (e.g., 50, FIG. 2A) can be dispensed with, simplifying IPG design and saving room within the interior of the case 12 and on the PCB 30 (FIG. 1C).

Microcontroller block 150 may receive interrupts independent of the bus 92 and its communication protocol, although interrupts may also be sent to the microcontroller 150 via the bus 92 as well. Even though ASIC 160 includes a microcontroller block 150, the ASIC 160 may still couple to an external bus 90, as shown in FIG. 4A. This can facilitate communications between the ASIC 160 and another device, such as a memory integrated circuit (not shown) or possibly another microcontroller device that might be coupled to the bus 90. Bus 90 can also facilitate communication between (master) ASIC 160 and another identically-constructed (slave) ASIC 160', shown in dotted lines in FIG. 4A. As described in the Background, use of an additional ASIC 160' allows the number of electrodes 16 the IPG 10 supports to be doubled, and many of the same off-bus connections 54 can be used as described earlier, and as described in the above-referenced ASIC Publications. In one example, the microcontroller block 150 can comprise circuitry from an ARM Cortex-M0+ Processor, which may be incorporated into the monolithic integrated circuit of the ASIC 160 by licensing various necessary circuits from the library that comprises that processor.

Figure 5C:
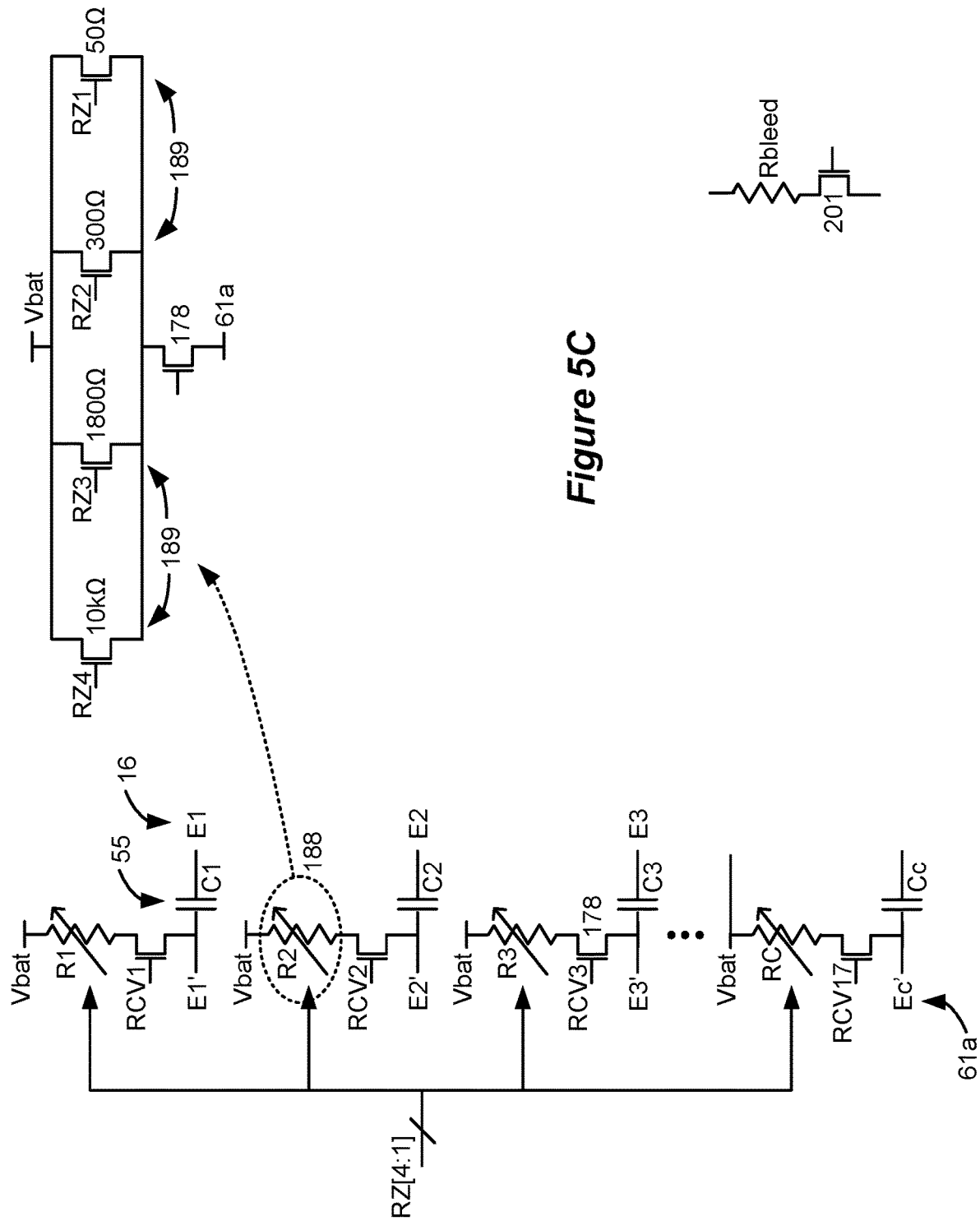

Improved architecture 140 comprises includes improved passive recovery circuitry used to remove charge on the DC-blocking capacitors 55, and FIGS. 5A-5C show specific circuitry details. By way of preview, the improved passive recovery circuitry allows for a greater deal of control regarding how passive recovery occurs. Passive recovery can be controlled in different modes, and can be controlled to provide different levels of resistance. Mode and resistance control are useful when operating the IPG 10 in different manners.

FIG. 5A shows an improved stimulation circuitry block 170 within ASIC 160, which can include improved DAC circuitry 172 (FIG. 4B) used to source or sink stimulation currents at the electrode nodes 61a via a PDAC 172p or NDAC 172n respectively. For simplicity, it is assumed that improved ASIC 160 supports sixteen electrode nodes 61a E1'-E16' coupleable to sixteen electrodes 16 E1-E16 used to stimulate a patient's tissue (e.g., on lead(s) 18; see FIG. 1A). However, this number of electrode nodes and electrodes is merely one example and other numbers could be used (e.g., 32, etc.).

Notice that the electrode nodes 61a can include the conductive case 12 of the IPG 10 (Ec), which improved ASIC 160 supports at electrode node Ec'. Thus, the case 12, like the electrodes 16, may comprise an actively controllable electrode from which a current can be sourced or sunk by connection to PDAC circuitry 172p or NDAC circuitry 172n, which is useful for monopolar stimulation, as is well known. PDAC and NDAC circuitry 172p and 172n can be as described earlier, or may take other forms, or may be as disclosed in U.S. Provisional Patent Application Ser. No. 62/393,003, entitled "Current Generation Architecture for an Implantable Medical Device," by inventors Pujitha Weerakoon, Goran N. Marnfeldt, and Philip L. Weiss, filed Sep. 10, 2016 (now U.S. Patent Application Publication 2018/0071520), and is incorporated by reference in its entirety. Note that PDAC 172p and NDAC 172n can comprise constant current sources or constant voltage sources.

Within improved stimulation circuitry block 170 is a recovery control block 174, which contains registers 175 that store data used to select different modes and resistances to be used during passive recovery. Recovery control block 174 and registers 175 implement logic that issue a number of control signals that are used to control passive recovery. Details concerning software and hardware used to populate the recovery control block 174 and registers 175 are discussed in detail in U.S. Provisional Patent Application Ser. No. 62/386,000, entitled "Pulse Definition Circuitry for Creating Stimulation Waveforms in an Implantable Pulse Generator," by inventors Philip Weiss, Goran Marnfeldt, and David Wagenbach, filed Sep. 10, 2016 (now U.S. Pat. No. 10,576,265), and is incorporated by reference in its entirety.

Control signals issued by recovery control block 174 include Rec[17:1], which indicate when passive recovery switches 178 (FIG. 5C) for the case (Rec17) and the electrodes E16-E1 (Rec16-Rec1) are to be turned on (i.e., closed). Control signal EnRec comprises a passive recovery enable signal, which as described below will enable control of the passive recovery switches 178. Control signal AllOn comprises a control signal that turns on all of the passive recovery switches 178, possibly even during stimulation, as described in detail later. Control signals Res[1:0] are used to control the resistance at which passive recovery occurs.

As shown, these control signals are issued to passive recovery logic 176, which is shown in further detail in FIG. 5B. Passive recovery logic 176 comprises various logic gates 182, 184, 185, and 186, which ultimately produce control signals RCV[17:1] that control the passive recovery switches 178 (FIG. 5C). Assertion of any of Rec1-Rec17 or AllOn indicates via OR gate 182 that at least one of the recovery switches 178 may be closed, and OR gate 182 indicates this fact ('1') to AND gate 184. If recovery switches are also enabled to be closed (EnRec='1'), then AND gate 184 indicates ('1') to AND gates 186 that at least one recovery switch 178 may be closed. Which of signals RCV1-RCV17 should be asserted to close which recovery switches 178, and with what timing, is dictated by Rec1-Rec17 and AllOn as received at OR gates 185. Again assuming that AND gate 184 has output a '1', if particular recovery control signals Rec1-Rec17 are asserted, then AND gates 186 will assert their corresponding control signals RCV1-RCV17, and thus close only the recovery switches 178 associated with those electrode nodes 61a E1'-E16' and Ec' respectively. If AllOn is asserted, OR gates 185 will then force AND gates 186 to assert all of control signals RCV1-RCV17, thus closing all of the recovery switches 178.

Also included in passive recovery logic 176 is a 2-to-4 demultiplexer (decoder) 180 which receives the resistance control signals Res1 and Res0 and generates four new resistance control signals RZ[4:1]. As will be explained below, each of the resistance control signals RZ4 to RZ1 sets a resistance for passive recovery, with RZ4 setting the highest resistance, and RX1 the lowest. Note that recovery control block 174 could issue resistance control signals RZ[4:1] directly, mooting the need for demultiplexer 180.

Figure 3:
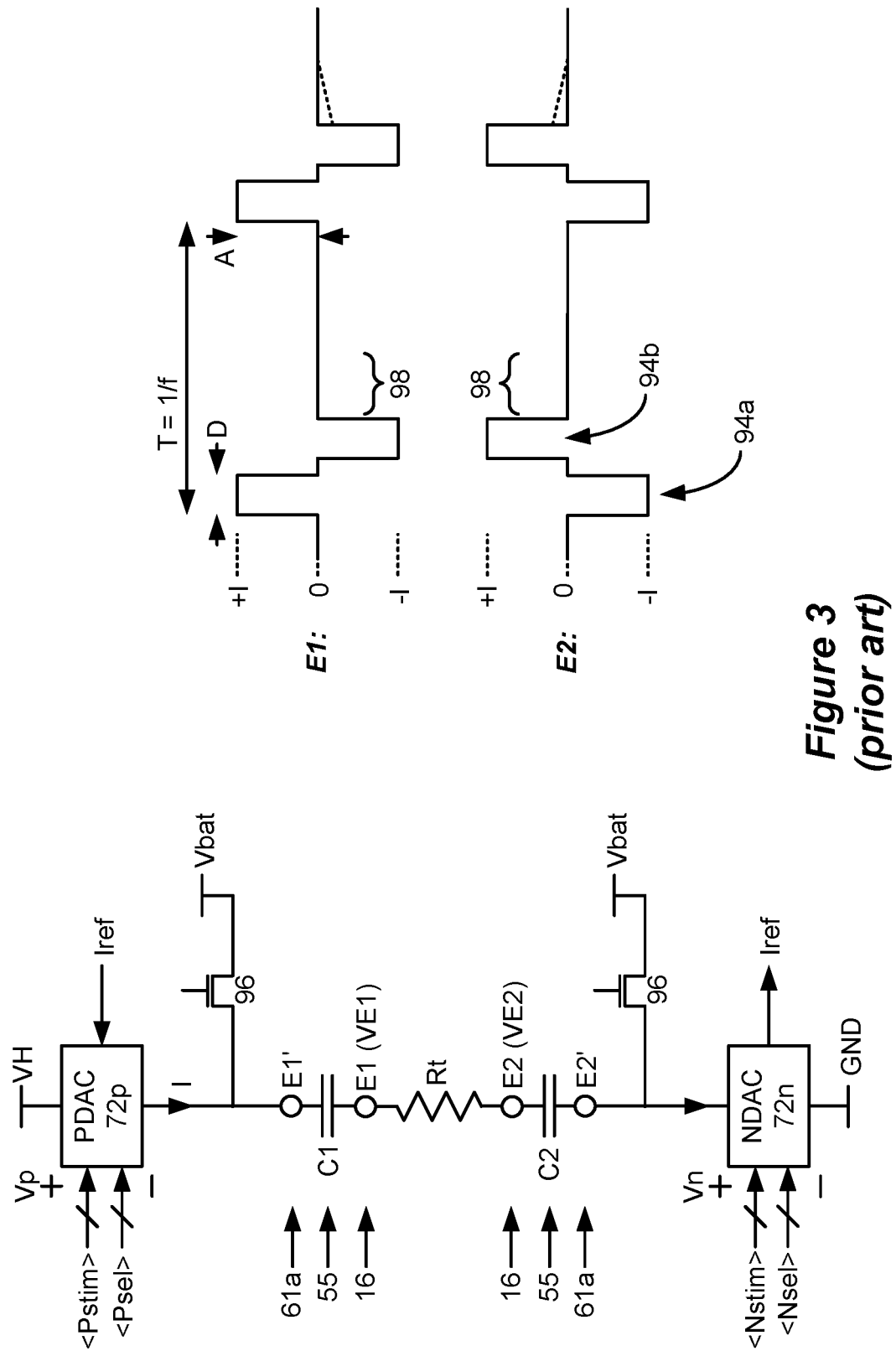
FIG. 3 shows aspects of the Digital-to-Analog converters within the stimulation circuitry of the ASIC, and stimulation pulses formable thereby, in accordance with the prior art.

FIG. 5C shows the passive recovery switches 178, which are similar to passive recovery switches 96 described earlier (FIG. 3) as they are connected between the electrode nodes 61a and a common reference voltage, such as Vbat. Other reference voltages could be used as well, such as the compliance voltage V+ described earlier, a midpoint voltage such as V+/2, ground (GND), or some other value. As noted earlier, each of the passive recovery switches 178 is controlled by one of the control signals RCV[17:1] issued by recovery logic 176.

In series with each of the passive recovery switches 178 are variable resistors 188, Rx, with each series connection being connected to one of the electrode nodes 61a, and the other end connected to a common reference voltage. Each of the variable resistors 188 receives each of the four resistance control signals RZ[4:1] described above, and thus any of these control signals can be asserted to set the resistance of all of the variable resistors 188. FIG. 5C shows the variable resistors 188 in one example, which comprises four resistance transistors 189 connected in parallel between the passive recovery switches 178 and the common reference voltage (e.g., Vbat). (The variable resistors 188 could also be placed between the passive recovery switches 178 and the electrode nodes 61a). Resistance control signals RZ[4:1] are each received at the gate of one of the resistance transistors 189. Each of resistance transistors 189 is preferably sized differently to provide a different resistance. This sizing difference can be realized by constructing each of the resistor transistors 189 with different lengths (e.g., 50×, 300×, 1800×, and 10000×), although the transistors widths could be sized as well. In the example shown, RZ1 controls a resistance transistor 189 of 50 ohms; RZ2 controls 300 ohms; RX3 controls 1800 ohms; and RZ4 controls 10000 ohms.

FIG. 6 shows different modes in which the improved recovery circuitry can be operated. Three operational modes, discussed further below, are shown in the three rows of FIG. 6, as are the control signals (EnRec, AllOn, Rec[17:1]) issued by recovery control block 174 used to enable these modes. Further included are different resistances (50, 300, 1800, and 10 k ohms) that can be selected through control of the resistance transistors 189 (RZx), each of which can be used with each mode. FIG. 6 also includes IPG use models in which particular modes and resistances will be beneficial. However, these use models are merely examples, and other use models known now or in the future may benefit from the flexibility that mode and resistance selection of the improved recovery circuitry can provide.

The modes and resistances shown in FIG. 6 may be intentionally selected. Normally such selection would be made by a clinician using software running externally on a well-known clinician's programming computer, which can wirelessly communicate the passive recovery selections (mode and resistance) to the IPG 10 for implementation in conjunction with one or more stimulation program (SP(s)). Stimulation program(s) may also be wirelessly communicated from the clinician's programmer, and more than one stimulation program may be run by the DAC circuitry 172 at a time on different timing channels, as is well known.

Alternatively, passive recovery modes and resistances may be automatically chosen by the IPG 10 depending on the one or more stimulation programs that are running in the IPG 10. For example, and referring to FIG. 5A, note that the stimulation program(s) can be reported from the DAC circuitry 172 to the recovery control block 174 used to generate the passive recovery control signals, thus enabling the recovery control block 174 to assist in automatic selection of the mode and/or resistance. However, recovery control block 174 may receive an indication of the IPG's stimulation program(s) in different manners, and so may automatically select a mode and/or resistance from such different manners.

Figure 7A:
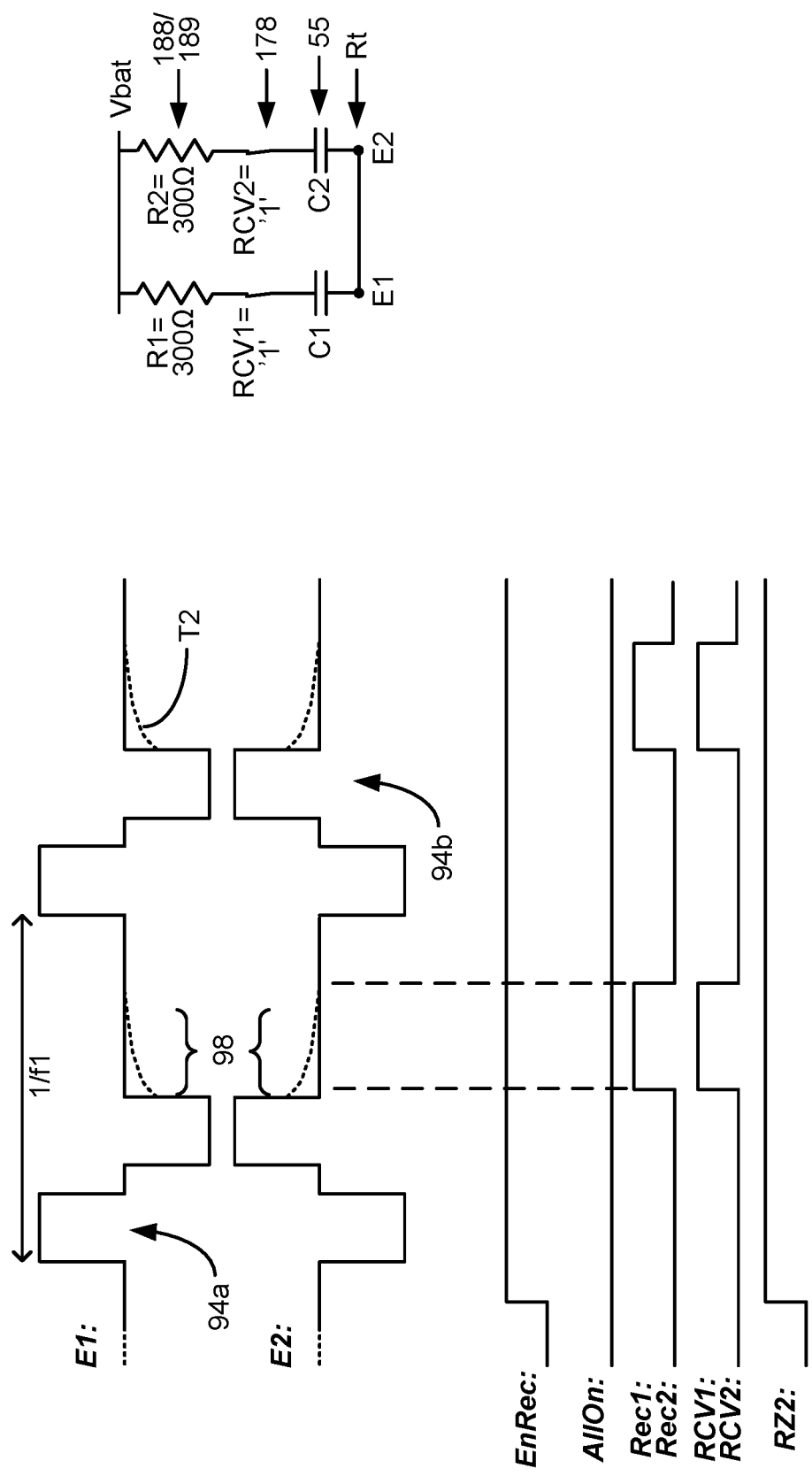
FIGS. 7A-7D show examples of various stimulation programs operating in different timing channels, and shows how the different modes and resistances operate, in accordance with examples of the invention.

Referring again to FIG. 6, in the first mode, the only passive recovery switches 178 that are closed are those associated with electrodes 16 that have been chosen for stimulation. This mode is shown first in FIG. 7A, showing an example stimulation program involving electrodes E1 and E2. As the waveforms in FIG. 7A show, electrodes E1 and E2 are selected to operate respectively as an anode and cathode during a first pulses phase 94a, with their polarity switching during a second pulse phase 94b. This however is merely one example of stimulation; any of the electrodes (including the case 12) can be selected to operate as an anode or cathode, and more than one anode or cathode can be selected to operate at a given time.

During this first mode, EnRec is asserted to enable passive recovery switches 178 to be closed, and AllOn is deasserted. Individual recovery control signals associated with selected electrodes E1 and E2, Rec1 and Rec2, are asserted by recovery control logic 174 (FIG. 5A) after conclusion of the second (last) pulse phase 94a, during passive recovery time period 98. The operation of recovery logic 176 (FIGS. 5A and 5B) asserts control signals RCV1 and RCV2 with the same timing as Rec1 and Rec2, which causes only passive recovery switches 178 coupled to electrode nodes E1' and E2' to close, as shown in FIG. 7A. All other passive recovery switches '78 (corresponding to RCV3-17; electrode nodes E3'-E16' and case electrode node Ec') are left open, as they were not involved in stimulation, and thus should not have significant charge built up on their DC-blocking capacitors 55 requiring recovery.

Notice also in FIG. 7A that the 300 ohm resistance transistors 189 have been selected as active (RZ2='1'). Thus, during period 98 when switches 178 corresponding to E1 and E2 are closed, DC-blocking capacitors 55 C1 and C2 are respectively placed in series with R1 and R2 equaling 300 ohms, with each series connection being connected in parallel between the common reference voltage (e.g., Vbat) and the previously-active electrodes E1 and E2, which are coupled through the patient's tissue, Rt. This will, over time period 98, passively equilibrate charge across capacitors C1 and C2 that may be remaining even after the second pulse phase 94b.

Notice in FIG. 7A that charge equilibration during passive recovery time period 98 can be represented by an exponentially-decaying waveform as shown in dotted lines. Such decay waveform may be increasing or decreasing, depending whether the net charge left on the capacitors C1 and C2 after the second pulse phase 94b was net negative or positive. The time-constant T2 of that exponentially-decaying waveform will be affected by the resistance chosen (i.e., 300 ohms). Because the resistance is relatively large (300 ohms), the time constant T2 will be relatively large, and hence passive recovery time period 98 must be relatively large to ensure that charge on the capacitors is recovered. As a result, use of the first mode, and selection of a larger resistance (RZ2=300 ohms) supports use of relatively low frequency stimulation (<f1) as depicted in FIG. 7A, and as reflected in the table of FIG. 6. Selection of even higher resistances 189 (RZ3=1800 ohms; RZ4=10 k ohms) would support even lower stimulation frequencies.

Figure 7B:
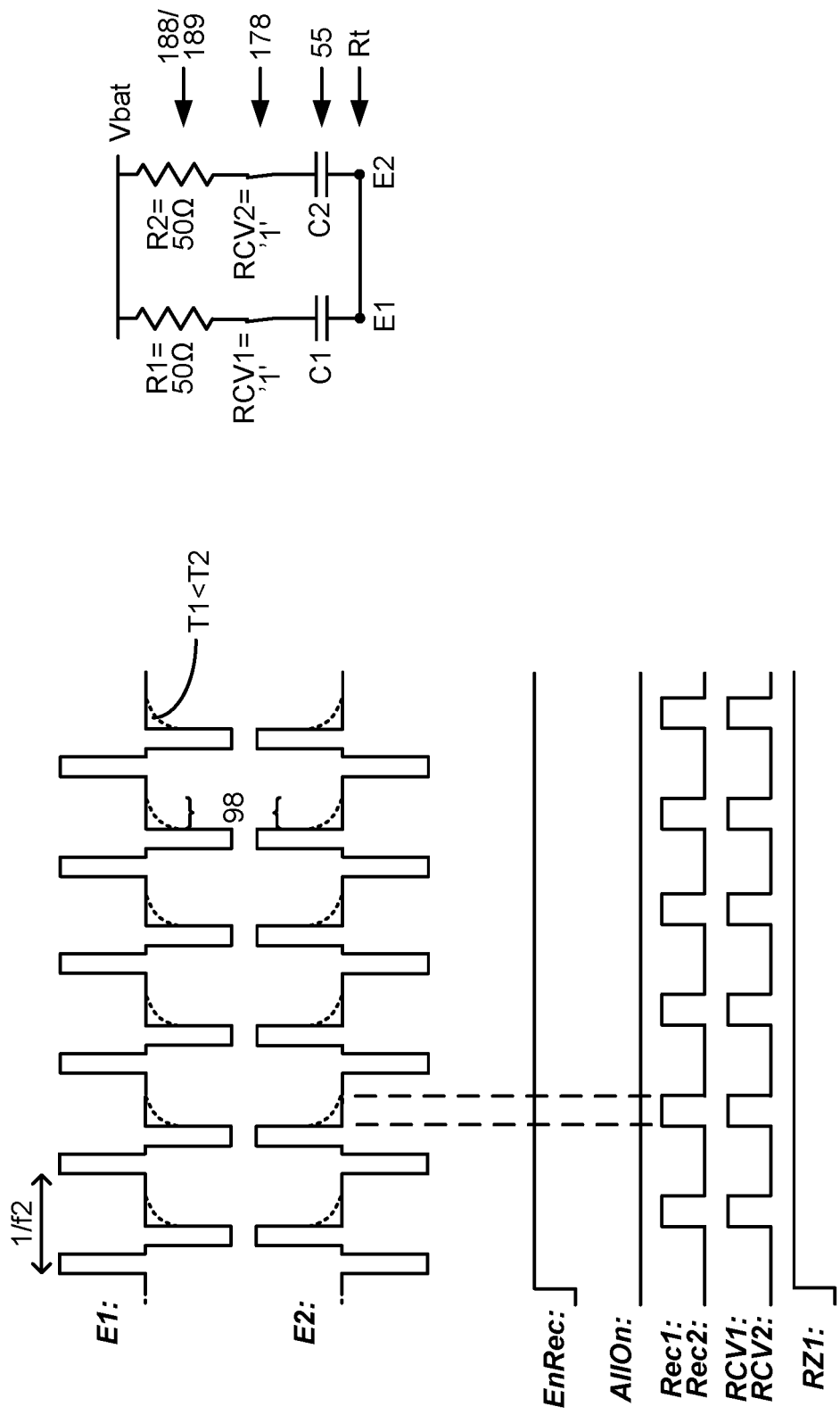

FIG. 7B provides another example of the first mode of passive charge recovery in which the only passive recovery switches 178 closed are those associated with electrodes 16 that have been selected for stimulation, which is again assumed to be electrodes E1 and E2. However, in this example, a lower value for the resistance of variable resistor 188 is chosen (i.e., RZ1, selecting 50 ohms). This decreases the time constant T1 of the circuit, which decreases the passive recovery period 98 and decreases the time that passive recovery switches 178 must be closed (per RCV1 and RCV2) after each preceding pulse (second pulse phase 94b). Because the time period 98 is decreased, a subsequent pulse (first pulse phase 94a) can be issued more quickly, meaning generally that the frequency of the stimulation pulses can be increased (e.g., f2>f1). Said differently, selection of a low-resistance resistance transistor 189 in the first mode can be beneficial for higher frequency stimulation.

Figure 7C:
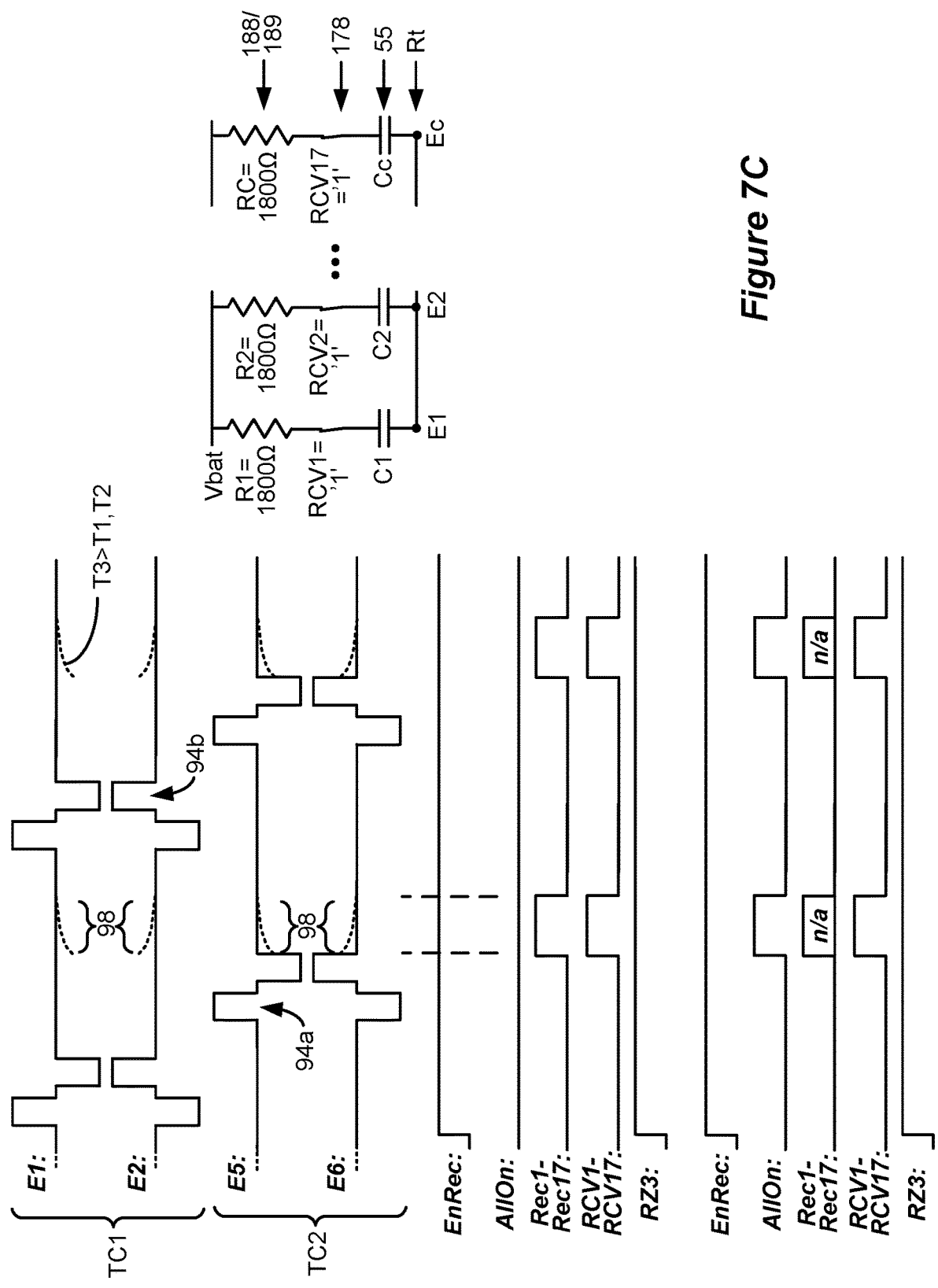

A second mode in which the improved recovery circuitry can be used is shown in the second row of FIG. 6, and involves closing the recovery switches of all of the electrodes in the IPG 10, regardless whether they have been selected for stimulation or not. As shown in the table of FIG. 6, this mode can be useful in one example if more than one timing channel (TC) is used for stimulation, as shown in FIG. 7C. The second mode could though also be useful in other contexts.

FIG. 7C shows a first timing channel (TC1) running a first stimulation program in which electrodes E1 and E2 have been selected. A second timing channel (TC2) runs a different stimulation program in which electrodes E5 and E6 are selected. Notice in this example that the pulses in timing channel TC2 issue after the pulses of TC1. In this circumstance, it may be convenient to simply close all of the recovery switches 178 during period 98 after TC2's pulses, thus passively recovering charge on all of the DC-blocking capacitors 55, including capacitors C5 and C6 associated with electrodes E5 and E6, and capacitors C1 and C2 associated with electrodes E1 and E2, which were stimulated earlier. This can occur because the passive recovery time period 98 after TC2's pulses ends before pulses in TC1 begin; thus, there is no risk that closing all recovery switches 178 will short out electrodes that might be active in the IPG 10 in another timing channel.

Control of the second mode can be implemented in a couple of different ways, as shown in FIGS. 6 and 7C. As with the first mode, EnRec is asserted to enable closing of the recovery switches 178. In a first example, control signal AllOn is deasserted, and closing of all recovery switches 178 occurs by simply asserting all of control signals Rec1-Rec17 during recovery periods 98 (after TC2's pulses). Per recovery logic 176 (FIG. 5B), this asserts RCV1-RCV17 during the recovery period, which closes all recovery switches 178, and results in the circuit shown in FIG. 7C. Note that DC-blocking capacitors 55 not currently involved in stimulation (e.g., C3, C4, C7, C8, etc.) are also tied in parallel, but this is not harmful, and further neutralizes any net charge on those capacitors. This is helpful should parasitic capacitances be present on those unselected capacitors; should those capacitors have a remaining net charge from previous use; or otherwise to simply prepare the electrodes associated with those unselected capacitors for future stimulation. Note also that a resistance of 1800 ohm (RZ3) has been chosen in FIG. 7C for passive recovery, although any other appropriate resistance (RZ1, RZ2, RZ4) could also be chosen.

A second example in which the second mode can be implemented is also shown in FIGS. 6 and 7C. In this example, control signal AllOn is asserted during recovery periods 98 (after TC2's pulses). Per recovery logic 176 (FIG. 5B), all of OR gates 185 and AND gates 186 would output a '1' during these periods, hence asserting all of control signals RCV1-RCV17 to close all of the recovery switches 178. In this example, the status of individual recovery signals Rec1-Rec17 issued by the recovery control block 174 are effectively overridden by AllOn, and hence their values are irrelevant.

Figure 7D:
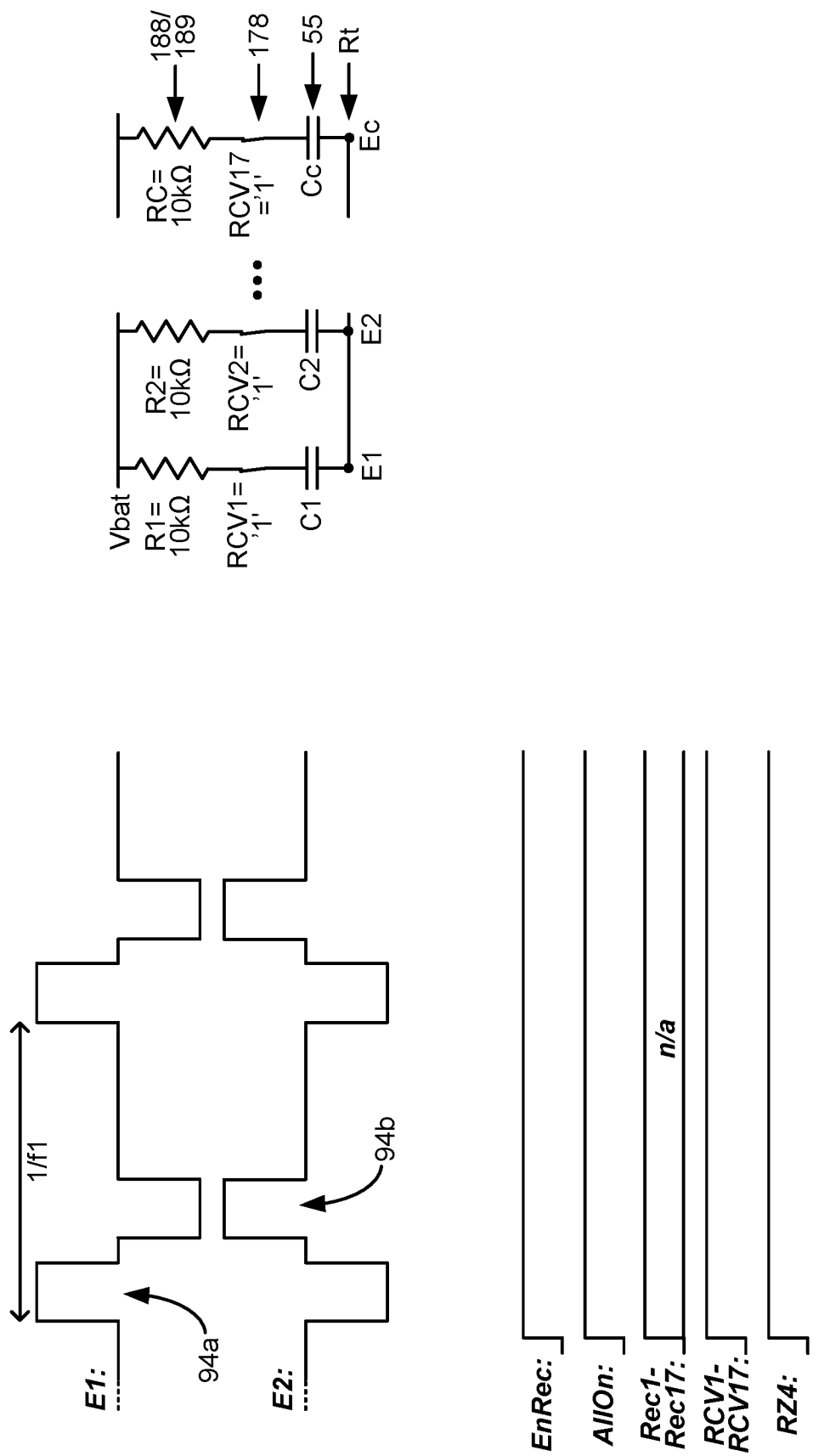

A third mode is illustrated in FIGS. 6 and 7D, in which all recovery switches 178 are turned on continuously. In this mode, EnRec is asserted to enable closure of the recovery switches 178, and AllOn is continually asserted to close all of the recovery switches 178 for an extended period of time. The statuses of control signals Rec1-Rec17 are irrelevant as AllOn effectively overrides them, as just explained.

This third mode can be used both when the IPG 10 is providing stimulation, and during periods of non-stimulation as well. For example, and as shown in FIG. 6, the third mode may be enabled to provide protection when the IPG is in certain environments, such as during certain procedures that may be performed on the IPG patient, such as electrocautery or MM. Both of these procedures involve the use of Radio Frequency (RF) fields, which can couple to the IPG 10's leads (18; FIG. 1A), and thus be presented to the IPG's internal circuitry. Closing all of the recovery switches 178 assists in protecting the IPG circuitry, because signals induced on the IPG leads 18 can be shunted to the common reference voltage (e.g., Vbat) through the switches. Selection of a low resistance 189 (RZ1=50 ohms) helps in this regard.

Additionally, and referring to FIG. 5C, a large resistance, Rbleed, which may be several Megaohms, may connect the battery voltage Vbat to the larger case 12 of the IPG 10, and may further be placed between any electrode node 61a and Vbat. The Rbleed resistances assist in dissipating shunted current, and mitigate the buildup of any unequal charge on capacitors of unused electrodes. Activation of the various Rbleed resistances can be assisted by a switch 201 connected serially to it, thus allowing Rbleed to shut off as necessary, such as during manufacturing to run various production leakage tests.

The third mode can also be used during active stimulation—that is, during the provision of stimulation pulses at the electrodes, as is shown in FIG. 7D. Even though a stimulation program is running using electrodes E1 and E2, AllOn is asserted during and between the pulses, and hence all recovery switches 178 are continually closed. Keeping the recovery switches 178 continuously closed continually passively recovers charge from all of the DC-blocking capacitors 55. Note that some of the stimulation current intended to reach the patient's tissue Rt (FIG. 3) from electrodes E1 and E2 during the pulses will instead be shunted to the common reference voltage (e.g., Vbat) through the closed recovery switches 178 (especially through the switches 178 coupled to electrode nodes E1' and E2'), and to ground through the bleed resistor Rbleed. However, such current loss can be mitigated through appropriate selection of the resistance transistor 189 (FIG. 5C) in series with the recovery switches 178. Specifically, in this third mode, when providing stimulation, it is desired to choose the highest resistance (RZ4=10 k ohms). As this resistance 189 is about an order of magnitude larger than the expected resistance of the patient's tissue Rt, therapeutic current loss through the recovery switches 178 is minimized. The high resistance of the bleed resistor Rbleed also helps to minimize current loss.

Use of the third mode during stimulation can be useful in a number of different examples. In one example, continuous charge recovery from all of the DC blocking capacitors can be useful during high frequency stimulation. As discussed earlier with respect to FIG. 7B, the time period 98 allowable for passive recovery between high frequency pulses may be short, and so continuously recovering charge in this third mode mitigates this problem.

While the improved passive recovery circuitry has been described as useful to recover charge from DC-blocking capacitors 55, this is not strictly necessary. Some IPG architectures may not use DC-blocking capacitors, yet may still have inherent capacitances that will charge as a stimulation current is provided. Such inherent capacitances may for example occur at various boundaries, such as the boundary between the electrodes and the patient's tissue. The improved recovery circuitry can be used to recover charge in such architectures, even though they lack intentionally-placed capacitances like the DC-blocking capacitors 55.

Although the variable resistor 188 is described as being comprised of four parallel-connected resistance transistors 189 (FIG. 5C) each controlled by a unique control signal (RZ1-RZ4), it should be understood that different numbers and configurations of transistors could be used. For example, two resistance transistors 189 can be used in parallel in the variable resistor 188, one of which is always on to provide a (default) high resistance, and another which is controlled by a single control signal. When the single control signal is asserted, the parallel connection of the transistors 189 will cause the resistance of the variable resistor 188 to decrease, hence enable two selectable resistances to be used for passive recovery with only a single control signal.

Although three modes of passive recovery switch control are disclosed, it should be understood that not all three modes may be necessary in a given implementation. Any two of the three modes may provide sufficient passive recovery control.

While disclosed in the context of an implantable pulse generator, it should be noted that the improved stimulation circuitry 170 and DAC circuitry 172 could also be implemented in a non-implantable pulse generator, such as an External Trial Stimulator (ETS). See, e.g., U.S. Pat. No. 9,259,574 (describing an ETS).

Although particular embodiments of the present invention have been described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A pulse generator, comprising:
   a plurality of electrode nodes, wherein each of the electrode nodes is configured to be coupled to a different electrode in contact with a patient's tissue;
   a common reference voltage;
   a plurality of switches, where each switch is configured to couple one of the electrode nodes to the common reference voltage;
   stimulation circuitry configured to concurrently provide stimulation pulses to two or more of the electrode nodes; and
   control circuitry configured to operate the plurality of switches in a first mode, a second mode, and a third mode, and to select operation in the first mode, the second mode, or the third mode,
      wherein in the first mode, the control circuitry is configured after each of the stimulation pulses to only close the switches associated with the two or more electrode nodes,
      wherein in the second mode, the control circuitry is configured after each of the stimulation pulses to close all of the switches, and
      wherein in the third mode, the control circuitry is configured to close all of the switches during and between the stimulation pulses.

2. The pulse generator of claim 1, further comprising a plurality of DC blocking capacitors, wherein each of the electrode nodes is configured to be coupled to its different electrode via one of the DC blocking capacitors.

3. The pulse generator of claim 1, wherein the two or more electrode nodes comprise less than a total number of the plurality of electrode nodes.

4. The pulse generator of claim 1, further comprising a plurality of variable resistors, each of the variable resistors having a variable resistance, wherein each of the switches is connected to a different one of the variable resistors, and wherein the control circuitry is further configured to select a resistance of each of the variable resistors.

5. The pulse generator of claim 1, wherein the control circuitry comprises a stimulation program used to concurrently provide the stimulation pulses to the two or more electrode nodes, wherein the control circuitry is configured to automatically select operation in the first, second, or third mode based upon the stimulation program.

6. The pulse generator of claim 1, further comprising a battery, wherein the common reference voltage comprises a voltage of the battery.

7. The pulse generator of claim 1, further comprising a conductive case, wherein one of the electrode nodes comprises a case electrode node configured to be coupled to the case.

8. The pulse generator of claim 1, further comprising at least one implantable lead, wherein the electrodes are located on the lead.

9. A pulse generator, comprising:
   a plurality of electrode nodes, wherein each electrode node is configured to be coupled to a different electrode in contact with a patient's tissue;
   a common reference voltage;
   a plurality of switches, where each switch is configured to couple one of the electrode nodes to the common reference voltage;
   stimulation circuitry configured to concurrently provide stimulation pulses to two or more of the electrode nodes; and
   control circuitry configured to close all of the switches during and between the stimulation pulses.

10. The pulse generator of claim 9, further comprising a plurality of DC blocking capacitors, wherein each of the electrode nodes is configured to be coupled to its different electrode via one of the DC blocking capacitors.

11. The pulse generator of claim 9, wherein the two or more electrode nodes comprise less than a total number of the plurality of electrode nodes.

12. The pulse generator of claim 9, further comprising a plurality of variable resistors, each of the variable resistors having a variable resistance, wherein each of the switches is connected to a different one of the variable resistors, and wherein the control circuitry is further configured to select a resistance of each of the variable resistors.

13. The pulse generator of claim 9, wherein the control circuitry comprises a stimulation program used to concurrently provide the stimulation pulses to the two or more electrode nodes, wherein the control circuitry is configured to automatically close all of the switches during and between the stimulation pulses based upon the stimulation program.

14. The pulse generator of claim 9, further comprising a battery, wherein the common reference voltage comprises a voltage of the battery.

15. The pulse generator of claim 9, further comprising a conductive case, wherein one of the electrode nodes comprises a case electrode node configured to be coupled to the case.

16. The pulse generator of claim 9, further comprising at least one implantable lead, wherein the electrodes are located on the lead.

* * * * *